United States Patent
MacCracken et al.

(10) Patent No.: US 6,683,641 B1
(45) Date of Patent: Jan. 27, 2004

(54) APPARATUS FOR INSPECTING THE INTERIOR OF HOLLOW ARTICLES

(75) Inventors: Brian MacCracken, Vernon, CT (US); William J. Habermann, Blairstown, NJ (US); Timothy J. Henry, Stroudsburg, PA (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 09/388,576

(22) Filed: Sep. 1, 1999

(51) Int. Cl.$^7$ ................................................ H04N 9/47
(52) U.S. Cl. ...................................... 348/82; 382/141
(58) Field of Search .............................. 348/82, 83, 84, 348/85, 90–95, 130–135; 250/223 B, 461.1; 382/141, 100; H04N 9/47

(56) References Cited

U.S. PATENT DOCUMENTS

| | | | |
|---|---|---|---|
| 4,628,207 A | 12/1986 | Elfert et al. | 250/461.1 |
| 4,642,526 A | 2/1987 | Hopkins | 315/244 |
| 4,675,728 A | 6/1987 | Egger et al. | 358/100 |
| 5,115,136 A | 5/1992 | Tomasch | 250/461.1 |
| 5,202,758 A | 4/1993 | Tamburrino | 358/98 |
| 5,449,919 A * | 9/1995 | Smart | 250/461.1 |
| 5,451,773 A * | 9/1995 | Triner et al. | 250/223 B |
| 5,563,417 A | 10/1996 | Gillard et al. | 250/461.1 |
| 5,619,587 A * | 4/1997 | Willoughby, Jr. et al. | 382/141 |
| 5,757,419 A * | 5/1998 | Queshi et al. | 348/82 |
| 5,879,289 A * | 3/1999 | Yarush et al. | 600/179 |
| 5,956,077 A * | 9/1999 | Qureshi et al. | 348/82 |
| 5,987,978 A * | 11/1999 | Whitehead | 73/146 |

* cited by examiner

Primary Examiner—Young Lee
Assistant Examiner—Tung Vo
(74) Attorney, Agent, or Firm—Kenneth C. Baran

(57) ABSTRACT

An apparatus for inspecting a selected target region in an interior cavity of a turbine engine rotor includes independent sources of ultraviolet and visible light for illuminating the selected target region, an arm having a working end translatable in a principal direction so that the working end is insertable into the rotor interior cavity, a primary camera mounted at the working end of the arm for capturing an image of the selected target region, a video monitor, and means for conveying the camera image from the primary camera to the video monitor. Ideally, the arm is also translatable in a secondary direction to facilitate positioning of the camera relative to the rotor. Suitable light guides convey the ultraviolet and visible light from their respective sources to the working end of the arm. A remote camera control, which is part of the camera electronics, allows an inspector to remotely focus the camera. An auxiliary viewing attachment with its own camera is reversibly securable to the working end of the arm for viewing surfaces angularly offset from the line of sight of the primary camera. The main components of the apparatus reside on a wheeled transport cart for easy portability.

14 Claims, 4 Drawing Sheets

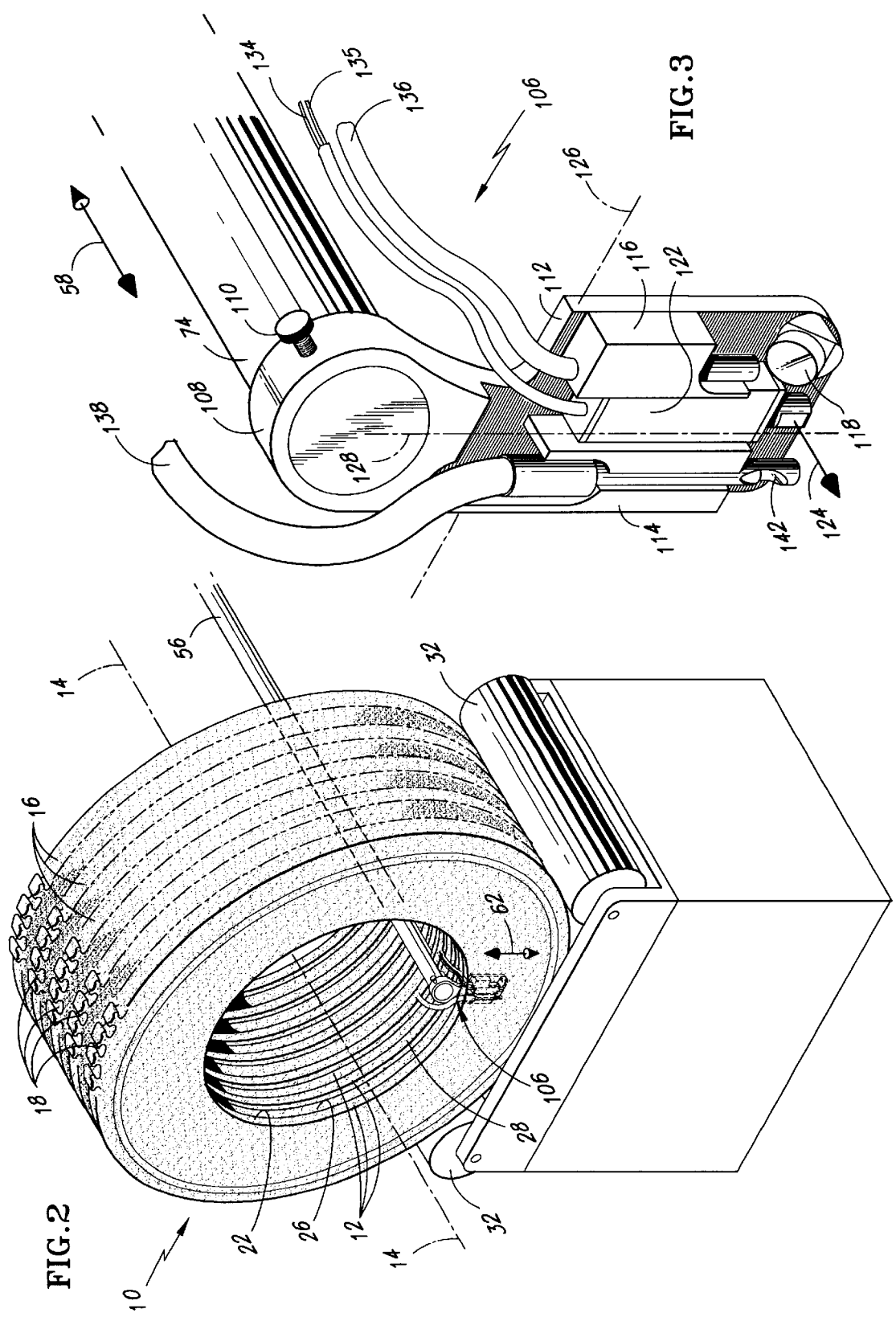

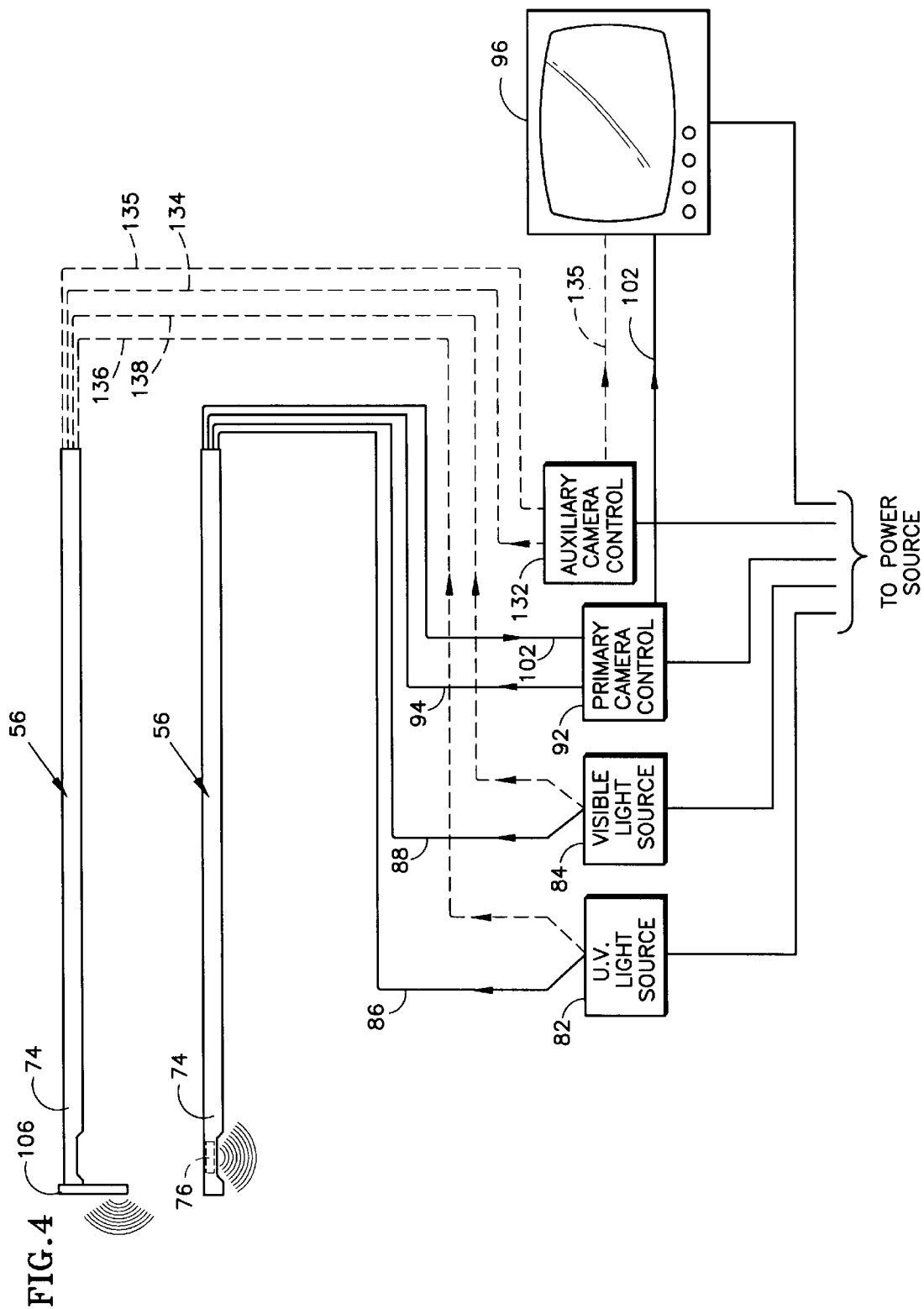

APPARATUS FOR INSPECTING THE INTERIOR OF HOLLOW ARTICLES

TECHNICAL FIELD

This invention pertains to an apparatus for conveniently carrying out a fluorescent inspection on the interior surfaces of a hollow article such as a gas turbine engine shaft or rotor assembly.

BACKGROUND OF THE INVENTION

Fluorescent penetrant inspection is a known technique for detecting surface cracks in metal articles. The fundamentals of fluorescent penetrant inspection are well known. A fluorescent penetrant is applied to the surface of interest. Excess penetrant coats the surface and seeps into any surface discontinuities such as scratches or cracks. Excess penetrant is then washed off the surface, leaving behind only residual penetrant trapped in the discontinuities. Upon exposure to ultraviolet (UV) light, the residual, entrapped penetrant fluoresces to reveal the presence of surface anomalies not discernible to the unaided eye. Subsequent examination of the surface under light in the visible portion of the spectrum is often necessary to determine if an anomaly is a potentially troublesome imperfection or merely an inconsequential scratch or other benign surface irregularity.

Fluorescent penetrant inspection is more complicated if the surface of interest is in the interior of a hollow article. Examples of such surfaces include the interior surfaces of gas turbine engine shafts, turbine rotors and compressor rotors. Specialized devices are required to view the surface and sometimes to apply the penetrant and wash away the excess.

One such specialized device is the apparatus described in U.S. Pat. No. 5,115,136. The apparatus includes appropriate light sources as well as canisters of penetrant, compressed air, water and a developer, all of which may be delivered to a desired inspection site by way of a fiberscope probe. The fiberscope also includes an eyepiece through which an inspector may view the site. Another specialized device is the borescope of U.S. Pat. No. 5,202,758. The described borescope includes means for determining the true physical size of a fluorescing anomaly. Despite the presumed merits of these devices, they are obviously hand-held, which makes it difficult for an inspector to obtain a steady, repeatable image or to view the image while engaging in related activities such as taking notes to record relevant observations or consulting manuals and instruction sheets. In addition, fiberscopes and borescopes of the type shown in the '136 and '758 patents have a narrow field of view, typically not much more than about four square centimeters, making it inordinately tedious to completely inspect a large surface.

U.S. Pat. No. 4,675,728 shows a device for inspecting the interior of pipes in a nuclear powerplant. The device is a carriage on wheels with a camera, appropriate light sources and a set of nozzles for directing fluorescent penetrant, water and air against an inspection site. The device is compact, having a height no more than about one third of the pipe diameter. In use, the device is inserted into the open end of a horizontal or inclined pipe with the carriage wheels contacting the pipe inner surface. The carriage is rolled along the pipe's relatively uninterrupted interior surface to the desired inspection site by way of an "umbilical cord" comprising the various cables and supply lines necessary to service the camera, lights and nozzles. Alternately, the device may be lowered, again by way of the umbilical, to a desired location within a vertical length of pipe.

Despite the presumed merits of the pipe inspection carriage, it is not without shortcomings. With the carriage positioned as shown in FIG. 2 of the '728 patent, only two 120° segments of the pipe are inspectable, and then only with a certain amount of disassembly and reassembly of the device's constituent parts. In addition, the device is ill suited for use in the interior of a turbine engine rotor assembly where the bores of axially successive rotor disks are separated by deep recesses. The axially alternating bores and recesses, unlike the axially uninterrupted inner surface of a pipe, would interfere with or prohibit rolling movement and precise positioning of the carriage. Even if a turbine engine rotor were oriented vertically (i.e. with its rotational axis vertical) and the pipe inspection apparatus lowered vertically into the rotor bore, it would be difficult to obtain a stable image of the inspection site because the inspection device would not be positively supported in the radial (horizontal) direction. Finally, the pipe inspection device is clearly adapted to treat and inspect only radially facing interior surfaces. No provisions are made to inspect surfaces at other orientations, for example the axially facing surfaces of a compressor or turbine disk.

Other types of illuminating and viewing devices may be of limited value because they include only a single, broad spectrum lamp with a single intensity adjustment. Such a lamp emits broad spectrum light comprising both ultraviolet and visible wavelengths. A filter capable of passing only the UV wavelengths is provided so that the device is operable in either a "pure UV" mode or in a "broad spectrum" mode depending on whether or not the filter is engaged. An inspection technician scans the surface of interest in the UV mode (i.e. with the filter engaged to pass only ultraviolet wavelengths). The technician typically conducts the UV inspection with the lamp intensity adjustment set at or near its maximum because the UV light emitted by commercially available lamps is relatively weak. If the technician observes a fluorescing anomaly, he switches to the broad spectrum mode because the non-fluorescing surroundings of the anomaly are not readily visible under the pure UV light. The technician needs to illuminate the immediate environs of the anomaly with visible light so that he can view the anomaly in the context of its surroundings and better judge its significance. Unfortunately, the visible light emitted by commercially available lamps is substantially stronger and brighter than the UV light. Therefore, if the technician engages the broad spectrum mode without first lowering the intensity adjustment of the lamp, the excessively brilliant visible light not only overpowers the fluorescence emitted by the anomaly, but also completely obstructs the technician's view of surface details that the visible light was intended to reveal. As a result, the anomaly is rendered temporarily indiscernible. Consequently, the technician is obliged to lower the intensity adjustment either before or after switching to the broad spectrum mode. However, lowering the intensity adjustment lowers the intensity of both the UV and the visible light, so that the visible light continues to overpower the fluorescence emitted by the anomaly. The absence of discernible fluorescence may cause the technician to lose track of the anomaly, forcing him to return to pure UV mode of illumination, raise the intensity adjustment to a higher level compatible with the weaker intensity pure UV light, and reacquire the anomaly. This obviously makes the technician's task tedious and frustrating, especially when the surface being inspected is large.

SUMMARY OF THE INVENTION

It is, therefore, a principal object of the invention to provide an inspection apparatus that facilitates convenient and thorough fluorescent penetrant inspection of the interior surfaces of hollow articles such as gas turbine engine shafts and rotor assemblies.

It is a corollary object of the invention to provide a stable, repeatable image of a target region within the article and to achieve a generous field of view.

It is another corollary object of the invention to enable convenient inspection of axially facing surfaces within the article.

It is another corollary object of the invention to inspect radially facing interior surfaces of the article over a full 360° of arc without the burden of reconfiguring the inspection apparatus.

It is another corollary object of the invention to inspect the interior of the article despite the presence of significant topographical irregularities such as the deep recesses between axially successive disks of a gas turbine rotor.

It is another corollary object of the invention to provide an apparatus and method by which selected target regions may be inspected without making repeated adjustments to the intensity of light illuminating the target and without significant risk of losing track of a fluorescing anomaly.

According to the invention, an apparatus for inspecting the interior surfaces of a hollow article includes a primary camera mounted at one end of a support arm for capturing a steady image of a target region to be inspected. The arm is translatable in a principal direction so that it may inserted into the interior of the article. The apparatus also includes ultraviolet and visible light sources for illuminating the target region and a video monitor for displaying the image.

According to one aspect of the invention, the light sources are independent sources with independent intensity adjustments so that the intensity of light emitted by either source can be adjusted without affecting the intensity of light emitted by the other source and so that an anomaly can be viewed simultaneously with both visible and UV light.

According to another aspect of the invention, the support arm is also translatable in a secondary direction perpendicular to the principal direction.

According to still another aspect of the invention, the apparatus includes an auxiliary viewing attachment, easily securable to the support arm. The auxiliary attachment has an auxiliary camera for viewing target regions angularly offset from the line of sight of the primary camera.

The invention is advantageous because it provides a stable, steady image of a target region inside a hollow article such as a turbine engine shaft or rotor assembly. The inventive apparatus also provides a generous, yet high resolution field of view since the cameras are mounted at an end of the arm proximate to the target region. The invention also offers 360° of viewing coverage since the article, if properly supported, may be rotated about the camera to bring different regions of the article's interior surface into the camera's field of view.

Another advantage is the ease with which the inventive apparatus can be adapted, by means of the viewing attachment, to view target regions angularly offset from the line of sight of the primary camera. In particular, the attachment is positionable in the deep annular recesses between neighboring rotor disks in a gas turbine compressor or turbine rotor to capture an image of the axially facing disk surfaces.

Another advantage is the ability of the apparatus to traverse the entire axial length of a rotor despite the presence significant topographical irregularities.

Another advantage of the invention is its ability to provide simultaneous illumination with both visible and ultraviolet wavelengths while minimizing the need for repeated light intensity adjustments.

These and other objects, features and advantages will become more apparent in light of the following description of the best mode for carrying out the invention and the accompanying drawings.

BRIEF DESCRIPTION OF THE DRAWINGS

FIG. 2 is a view similar to that of FIG. 1 showing the apparatus with an auxiliary viewing attachment secured thereto and being used to inspect an axially facing surface of one of the rotor disks.

FIG. 3 is an enlarged view of the auxiliary viewing attachment.

FIG. 4 is a schematic view showing the principal components of the inventive inspection apparatus and their interrelationships with each other.

BEST MODE FOR CARRYING OUT THE INVENTION

Figure 1:
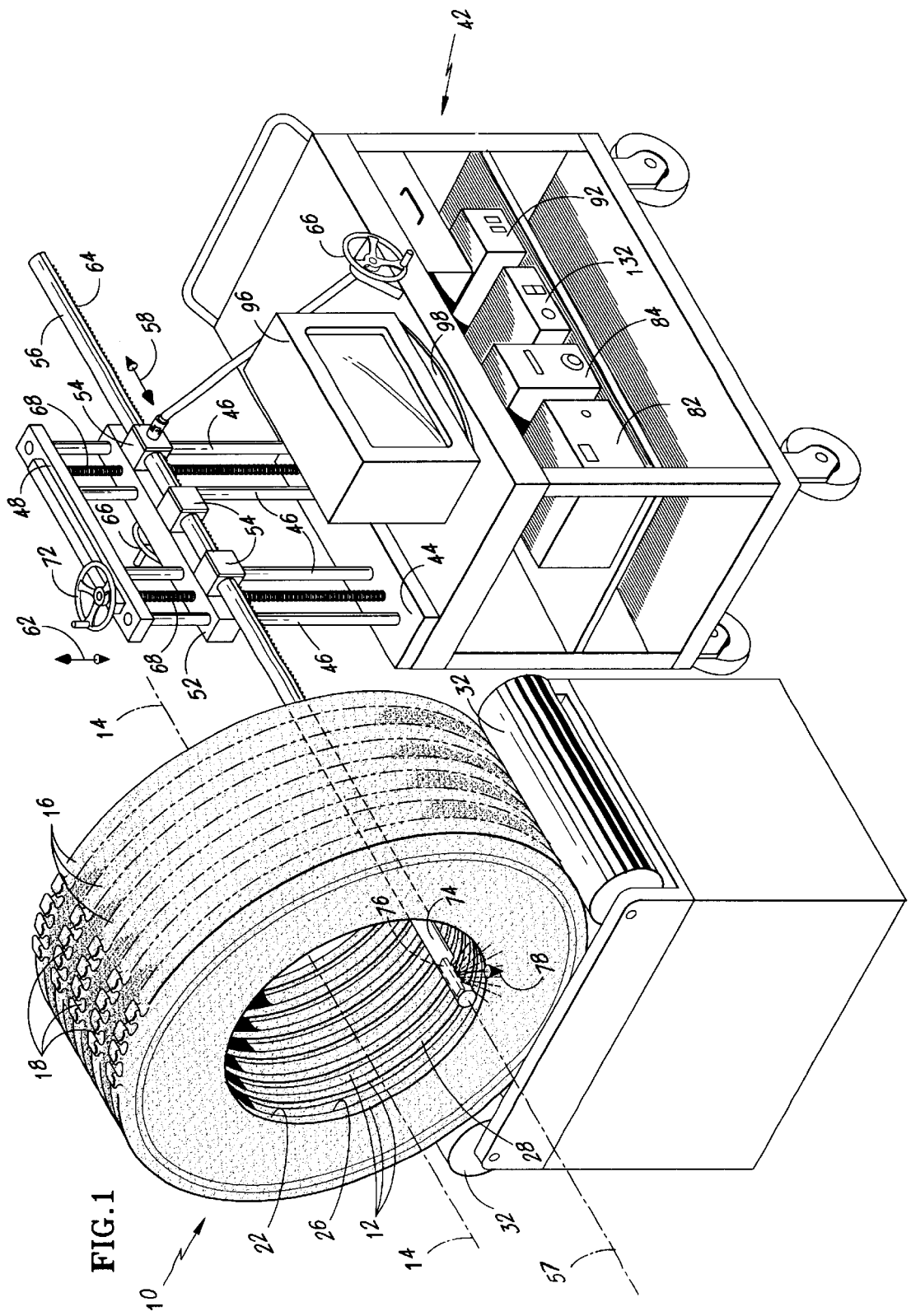
FIG. 1 is an overall perspective view of the inspection apparatus of the present invention being used to inspect the interior surface of a schematically illustrated turbine engine rotor assembly comprising multiple rotor disks.

FIGS. 1, 5, 6 and 7 schematically illustrate a rotor assembly 10 representative of a compressor or turbine rotor for a gas turbine engine. The rotor comprises multiple disks 12 disposed about a common rotational axis 14. Each disk has a rim 16 with a set of peripheral slots 18 for holding turbomachinery blades (not shown) and a radially inwardly extending hub 22 with axially facing surfaces 24. Each disk is secured to a neighboring disk by a mechanical attachment means or by a metallurgical bond joint near the disk rims 16. In the completed rotor assembly, the bores of axially successive disk hubs are separated by from each other by deep recesses 26 that extend radially from the bores of the hubs to the rotor rim. Accordingly, interior cavity 28 of the rotor assembly has a highly irregular topography. The illustrated rotor rests on a set of rollers 32 so that the rotor may be rotated about its axis 14.

During both original manufacture of the rotor and periodically throughout the rotor's useful life it is necessary to inspect the interior surface 34 of the rotor rim, especially the bond joints between neighboring disks, as well as the disk faces 24 for cracks or other surface flaws. These inspections can be effectively accomplished by conventional fluorescent penetrant inspection (FPI). The basics of FPI are well known. A technician prepares the rotor by applying a fluorescent penetrant to the surfaces of interest, and later cleansing the surfaces of excess penetrant. Residual penetrant remains trapped in any cracks or similar surface anomalies. The technician then exposes the surface to ultraviolet light, which causes the residual penetrant to fluoresce, revealing the presence of the anomaly. The technician may then expose the surface to visible light to get a better contextual view of the surface and determine if the anomaly is a genuine crack or merely a benign surface irregularity.

FIGS. 1 and 4 illustrate an apparatus for illuminating and viewing the interior surfaces of shafts and rotors. The principal components of the apparatus, which are described in more detail below, reside on a wheeled transport cart 42. The cart itself includes a frame comprising a base 44 affixed to the cart, guide posts 46 that extend vertically from the base, a horizontal support member 48 that interconnects the guide posts, and a vertically movable platform 52 with a set of three receptacles 54 extending therefrom.

The inspection apparatus includes an arm 56 that projects through openings in the receptacles 54. Mechanisms are provided to translate the arm in a principal direction 58 (i.e. horizontally) and preferably also in a secondary direction 62 perpendicular to the principal direction (i.e. vertically). The horizontal translation mechanism is a rack and pinion arrangement comprising pinion gears (not visible) housed inside one or more of the receptacles 54 and meshed with corresponding teeth 64 on the arm. Each pinion gear is rotatable by either of two cranks 66 to advance or retract the arm in the horizontal direction. The vertical translation mechanism is a leadscrew arrangement. The leadscrew arrangement includes a pair of leadscrews 68, each of which extends from the frame base 44 to the horizontal support member 48. The leadscrews project through internally threaded openings in the frame platform 52. The threads of the leadscrews engage the internal threads of the platform so that rotation of crank 72 raises or lowers the platform and the arm. The two leadscrews 68 are coupled together by a drive belt, not visible, so that rotary motion of either leadscrew is duplicated by the other leadscrew.

Figure 5:
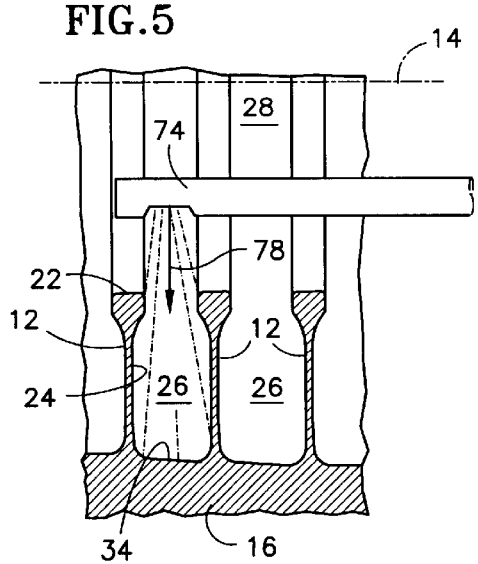
FIG. 5 is a schematic side elevation view showing the apparatus being used to inspect a radially facing inner surface of a turbine engine rotor.

The arm has a working end 74, which is insertable into the interior cavity 28 of the rotor by operating either of cranks 66. A primary camera 76 is mounted at the working end of the arm. The camera has a fixed orientation relative to the arm so that the camera's line of sight 78 is substantially perpendicular to the principal direction, i.e. radially oriented, for capturing an image of a selected target region on a radially facing surface, such as rotor rim interior surface 34 (FIG. 5). The arm could be made rotatable about an axis 57 so that the camera can survey a complete 360° arc. However, for inspecting the interior surfaces of a turbine engine rotor, such rotatability may be an unnecessary complication because alternate target regions can be brought into the camera's field of view by rotating the rotor about axis 14.

The apparatus also includes an ultraviolet light source 82 and an independent, visible light source 84 for illuminating a selected target region on the interior of the rotor assembly with ultraviolet and visible light respectively. The ultraviolet light source 82 produces broad spectrum light comprising ultraviolet wavelengths (shorter than about 390 nanometers) visible wavelengths (from about 390 to about 770 nanometers) and infrared wavelengths (longer than about 770 nanometers). However, the unit includes a 390 nanometer low pass filter that passes only the ultraviolet wavelengths so that the unit is useful as a source of ultraviolet light. Each light source has a power switch and intensity control for independently controlling the intensity of light emitted thereby.

In principle, the light sources could be integrated into the working end of the arm instead of being remote from the working end as shown. However remote placement of the sources is advantageous to minimize the amount of weight carried by the arm and to conserve space at its working end 74. As a result, the arm is radially compact so that it is insertable into small diameter openings. A liquid light guide 86 and a fiber optic light guide 88 convey ultraviolet and visible light from the respective light sources 82, 84 to the working end of the arm where the ultraviolet and visible light are directed substantially perpendicularly to the principal direction (i.e. parallel to the line of sight 78 of the primary camera) to illuminate the radially facing surfaces in the camera's field of view.

The apparatus also includes a primary camera control 92 for remotely focusing the primary camera 76. A manually operated switch on the camera control enables the inspection technician to send focusing commands to the camera by way of signal conductor 94.

The inspection apparatus also includes a video monitor 96 resting on a swivel table 98 for displaying the image of the target region captured by the primary camera. The monitor has two channels, "A" and "B" for receiving a primary video signal and an auxiliary video signal. The apparatus also includes means for conveying a video signal, and therefore the camera image, from the primary camera to the video monitor. In the illustration, the image conveying means is a signal conductor 102 extending from the camera to channel "A" of the monitor by way of the primary camera control 92, which is part of the camera electronics. Preferably, a conventional roof prism (not illustrated) is used to counteract image reversal effected by the camera optics so that the image displayed on the monitor is not inverted relative to the actual image.

In practice, the rotor assembly is coated with a fluorescent penetrant and then cleansed of excess surface penetrant to prepare the rotor for inspection. The specifics of preparing the rotor are not embraced by the present invention and the exact procedures may vary depending on the article to be inspected and the preferred practices of a given inspection facility.

The prepared rotor is rotatably supported on rollers 32. The inspection technician operates one of the cranks 66 to translate the arm 56 in the horizontal direction and thereby insert the working end 74 of the arm into the rotor cavity 28. The inspector continues to advance the arm into the cavity until the line of sight of the primary camera is axially aligned with a radially facing target region of interest. During this preliminary operation to position the primary camera, the technician may use the visible light source to illuminate the interior of the rotor. The technician may also operate crank 72 to move the camera radially thereby achieving optimum illumination of the target region and may also operate the remote camera control 92 to bring the target region into sharp focus. Once the camera is satisfactorily positioned, the technician shuts off any visible light that had been in use to facilitate camera positioning. The absence of visible light is important to ensure that fluorescence emitted by any surface anomalies is readily apparent.

With the camera satisfactorily positioned, the technician turns on the ultraviolet light source 82 to illuminate the selected target region with ultraviolet light. The technician adjusts the ultraviolet light intensity and selects an intensity strong enough to cause any residual penetrant to fluoresce. No further adjustments to the ultraviolet light intensity are required throughout the balance of the inspection. Upon detecting fluorescence, the technician turns on the visible light source to illuminate the target region with visible light. The technician then increases the intensity of the visible light, as necessary, so that the target region is sufficiently illuminated with visible light to enable him to establish the cause of the fluorescence. The technician may increase the visible light to an intensity high enough to overpower the fluorescence and render it indiscernible. Ideally, however, the technician uses a lower visible light intensity so that the fluorescence remains discernable. Accordingly, the technician can keep track of the fluorescing anomaly while simultaneously viewing it in the context of its surroundings.

Once the target region has been examined, the technician then continues to survey the interior surface by rotating the rotor about axis 14 to bring an alternate target region into the camera's field of view. The technician also extinguishes the visible light, but not the ultraviolet light, because the visible light can de-emphasize any fluorescence emitted by an anomaly in the alternate target region. If fluorescence is present in the alternate target region, the technician merely turns on the visible light and increases its intensity enough to view the fluorescing anomaly in the context of its surroundings.

The technician repeats the steps of illuminating a target area with ultraviolet light, examining the ultravioletly illuminated target, conditionally illuminating the target with visible light in the presence of ultraviolet light and extinguishing the visible light until his survey of the surface of interest is complete.

Referring now to FIGS. 2, 3, 4, 6 and 7, but primarily to FIG. 3, the inspection apparatus also includes an auxiliary viewing attachment 106 securable to the working end of the arm for viewing surfaces, such as disk faces 24, angularly offset from the primary camera line of sight. The attachment has a mounting collar 108 that slips over the working end of the arm and is secured in place by force fit or a thumbscrew 110. The attachment also has a support pad 112 with light guide brackets 114, 116, a reflector 118 and an auxiliary camera 122 affixed thereto.

With the viewing attachment secured to the arm, the auxiliary camera 122 has a line of sight 124 angularly offset from the primary camera line of sight. The auxiliary camera line of sight is at a fixed orientation relative to the attachment. The attachment, once secured to the arm 56 also has a fixed orientation relative to the arm. The auxiliary camera line of sight could be made variable, for example by providing one or more pivotable joints allowing the mounting pad to pivot relative to the collar about horizontal and/or vertical axes 126, 128. However, for inspecting the interior surfaces of a turbine engine rotor, a variable line of sight is an unnecessary complication. The auxiliary camera of the illustrated attachment has a line of sight oriented perpendicularly to the primary camera line of sight, i.e. parallel to the principal direction 58. As seen best in FIGS. 6 and 7, the attachment is reversible so that the line of sight 124 may be reoriented 180° about axis 128.

The apparatus also includes a remote auxiliary camera control 132 for remotely focusing the auxiliary camera. A manually operated switch on the auxiliary camera control enables the inspection technician to send focusing commands to the auxiliary camera by way of signal conductor 134.

The apparatus also includes a means for conveying a video signal, and therefore the image captured by the auxiliary camera, to the video monitor 96. In the illustration, the image conveying means is a signal conductor 135 extending from the auxiliary camera to channel "B" of the monitor by way of the auxiliary camera control 132 which is part of the camera electronics.

The viewing attachment also includes an auxiliary liquid light guide 136 and a fiber optic light guide 138 to convey ultraviolet and visible light from the respective light sources 82, 84 to the viewing attachment. The input end of each light guide is connected to the appropriate light source 82, 84 in lieu of the light guides 86, 88. The output end of each auxiliary light guide is clamped into the corresponding bracket 114, 116 on the viewing attachment. suitable reflectors 118, 142 direct the light in a direction substantially parallel to the auxiliary camera line of sight 124 to illuminate axially facing surfaces in the camera's field of view.

Figure 6:
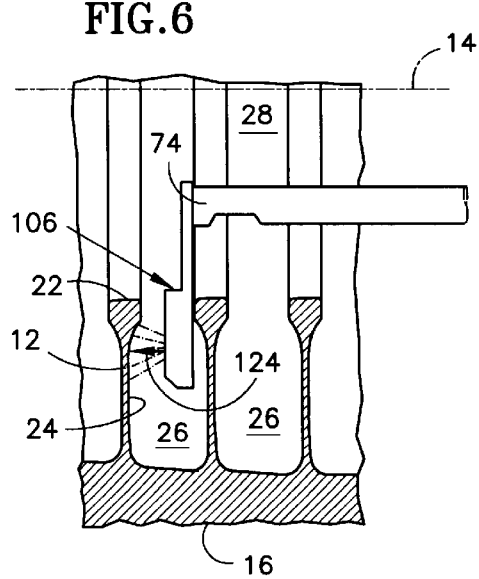
FIGS. 6 and 7 are schematic side elevation views showing the apparatus with the auxiliary viewing attachment secured thereto and being used to inspect axially facing surfaces in the interior of a turbine engine rotor.
Figure 7:
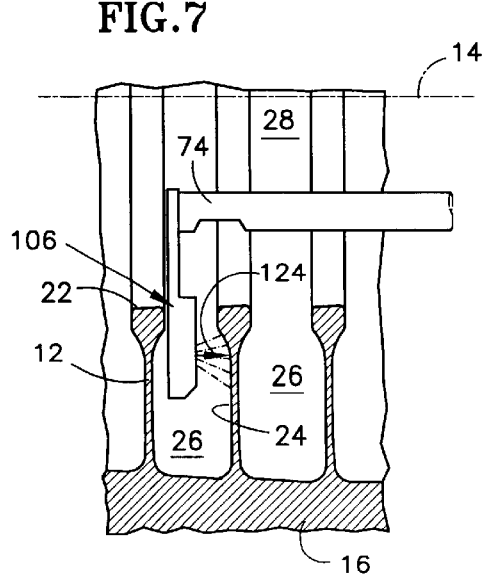

To use the auxiliary viewing attachment, the inspection technician merely slips the mounting collar 108 over the working end 74 of the arm 56, disconnects the light guides 86, 88 from the light sources 82, 84, and connects the auxiliary light guides 136, 138 to the sources. The technician advances the arm into the interior of the drum with the arm vertically positioned so that the viewing attachment clears the rotor bore. When the technician observes that the attachment is axially aligned with a selected recess 26 he operates the vertical translation mechanism to position the attachment in the recess as seen in FIGS. 2, 6 and 7. The technician may then commence inspection of axially facing target regions on the disk face 24 using the techniques already described in connection with inspecting the radially facing surfaces. To move the auxiliary camera's field of view in the radial direction, the technician simply operates the vertical translation mechanism. To view alternate target regions around the circumference of the disk, the technician rotates the rotor about axis 14.

The above-described apparatus overcomes the disadvantages of prior art devices. The arm 56 holds the cameras 76, 122 steadily at any desired position within the rotor cavity 28 to provide a stable, repeatable image of a selected target region. Moreover, the cameras provide a wide field of view (approximately 58 square centimeters for the primary camera and 22 square centimeters for the auxiliary camera) superior to that of a conventional borescope. Axially facing surfaces may be conveniently viewed with the viewing attachment 106. A full 360° of coverage can be achieved by merely rotating the rotor 10 about its axis. Because the arm 56 does not contact the interior surfaces of the rotor it can easily traverse the axial length of the rotor and can be precisely positioned despite the topographical irregularities represented by the axially alternating disk bores and recesses. Finally, the independent light sources with independent intensity adjustments minimize the tedium and frustration associated with prior art devices having only a single broad spectrum light source with a single intensity adjustment.

Although the invention has been presented in the context of fluorescent penetrant inspection, it is also useful for other fluorescent inspections such as fluorescent magnetic particle inspection. In a fluorescent magnetic particle inspection, a workpiece is temporarily magnetized and then treated with a fluorescent solution bearing metallic particles. The magnetized character of the workpiece causes the particles to become aligned in the vicinity of a surface anomaly in a way that emphasizes the presence of the anomaly.

Although the invention has been described with reference to a preferred embodiment thereof, those skilled in the art will appreciate that various changes, modifications and adaptations can be made without departing from the invention as set forth in the accompanying claims.

What is claimed is:

1. An apparatus for inspecting a selected target region in an interior cavity of a workpiece, comprising:
 a source of ultraviolet light for illuminating the selected target region;

a source of visible light for illuminating the selected target region;

an arm having a working end and translatable in a principal direction whereby the working end is insertable into the interior cavity of the workpiece, the arm also being translatable in a secondary direction perpendicular to the principal direction;

a primary camera mounted at the working end of the arm for capturing an image of the selected target region;

a video monitor; and means for conveying the image from the primary camera to the video monitor.

2. The apparatus of claim 1 wherein the ultraviolet light source and the visible light source are independent sources and the intensity of light emitted from the sources is independently adjustable.

3. The apparatus of claim 1 comprising a remote camera control for remotely focusing the primary camera.

4. The apparatus of claim 1 wherein the light sources are remote from the working end of the arm and the apparatus comprises an ultraviolet light guide and a visible light guide extending respectively from the ultraviolet and visible light sources to the working end of the arm for conveying light to the working end of the arm and illuminating the selected target region.

5. The apparatus of claim 1 wherein the primary camera has a line of sight substantially perpendicular to the principal direction.

6. The apparatus of claim 1 wherein the primary camera has a line of sight and the apparatus comprises a viewing attachment securable to the working end of the arm, the attachment including an auxiliary camera having a line of sight angularly offset from the primary camera line of sight for capturing an image of the selected target region.

7. The apparatus of claim 7 wherein the light sources are remote from the working end of the arm, comprising:

an auxiliary ultraviolet light guide for conveying ultraviolet light from the ultraviolet light source to the viewing attachment for illuminating the selected target region; and an auxiliary visible light guide for conveying visible light from the visible light source to the viewing attachment for illuminating the selected target region.

8. The apparatus of claim 6 comprising a remote auxiliary camera control connected to the auxiliary camera for remotely focusing the auxiliary camera.

9. The apparatus of claim 6 comprising means for conveying the image from the auxiliary camera to the video monitor.

10. The apparatus of claim 6 wherein the auxiliary camera line of sight is substantially perpendicular to the primary camera line of sight.

11. The apparatus of claim 6 wherein the viewing attachment is reversible to reorient the auxiliary camera line of sight 180°.

12. The apparatus of claim 6 wherein the viewing attachment comprises a collar for securing the attachment to the arm.

13. A method for inspecting an interior surface of a workpiece, the surface having been prepared for fluorescent inspection, comprising:

illuminating a selected target region of the surface with ultraviolet light of a selected intensity;

examining the ultravioletly illuminated selected target region and, upon detecting fluorescence, illuminating the selected target region with visible light in the presence of the ultraviolet light;

adjusting the intensity of the visible light, as necessary, so that the selected target region is sufficiently illuminated with the visible light to establish the cause of the fluorescence;

extinguishing the visible light; and repeating the steps of illuminating with ultraviolet light, examining the ultravioletly illuminated selected target region, conditionally illuminating the target with visible light and adjusting the intensity of the visible light on successively selected target regions without further adjustments to the intensity of the ultraviolet light until the surface of interest has been satisfactorily surveyed.

14. The method of claim 13 wherein the fluorescence remains discernible upon conclusion of the adjusting step.

* * * * *